United States Patent [19]

Sheehan et al.

[11] Patent Number: 5,087,772

[45] Date of Patent: Feb. 11, 1992

[54] METHOD FOR PREPARING 4-HYDROXYSTYRENE

[75] Inventors: Michael T. Sheehan, Corpus Christi, Tex.; Lan Shen, Riehen, Switzerland

[73] Assignee: Hoechst Celanese Corporation, Somerville, N.J.

[21] Appl. No.: 614,767

[22] Filed: Nov. 16, 1990

[51] Int. Cl.$^5$ .................. C07C 37/11; C07C 39/20
[52] U.S. Cl. ................. 568/804; 524/460; 568/716; 568/780; 568/781; 568/785; 568/790
[58] Field of Search ............ 568/790, 780, 781, 785, 568/804, 782, 783, 784, 785, 786, 787, 788, 789, 790, 791, 792, 793, 794, 716; 524/460

[56] References Cited

U.S. PATENT DOCUMENTS

| 4,316,995 | 2/1982 | Pittet et al. | 568/780 |
|---|---|---|---|
| 4,678,843 | 7/1987 | Elmore et al. | 525/378 |
| 4,689,371 | 8/1987 | Elmore et al. | 525/374 |
| 4,822,862 | 4/1989 | Rupp et al. | 525/367 |
| 4,898,916 | 2/1990 | Gupta et al. | 525/344 |
| 4,912,173 | 3/1990 | Keene et al. | 525/378 |
| 4,962,147 | 10/1990 | Vicari | 524/460 |

OTHER PUBLICATIONS

"Preparation of Vinylphenols and Isoprophenols", Corson et al., vol. 23, 1958, *J. Org. Chem.*
U.S. patent application No. 221,145 filed Jul. 7, 1988, by Shah et al.

*Primary Examiner*—Werren B. Lone
*Attorney, Agent, or Firm*—Jerome Rosenstock; Shirley L. Church

[57] ABSTRACT

A method for preparing 4-hydroxystyrene is disclosed. The method comprises reacting 4-acetoxystyrene with a suitable alcohol in the presence of a catalytic amount of a suitable base.

7 Claims, No Drawings

METHOD FOR PREPARING 4-HYDROXYSTYRENE

BACKGROUND OF THE INVENTION

1. Field of the Invention

This invention relates to a method for preparing 4-hydroxystyrene, and more particularly for preparing 4-hydroxystyrene by reacting 4-acetoxystyrene with a suitable alcohol in the presence of a catalytic amount of a suitable base.

2. Description of the Prior Art

4-Hydroxystyrene is a well-known compound which is itself useful as a food flavoring substance and as an intermediate in the preparation of polymers and copolymers useful in coatings, electronic applications, ion exchange resins, photoresists, etc.

Although there are several known ways to prepare 4-hydroxystyrene, these known methods are not commercially feasible in the further utilization of the 4-hydroxystyrene. The 4-hydroxystyrene itself is difficult to isolate, since it (1) readily decomposes, (2) is toxic via skin absorption, and (3) readily polymerizes and as a result, those skilled in the art have made numerous attempts to find a method of synthesizing 4-hydroxystyrene in a manner which avoids polymerization and provides the 4-hydroxystrene in a medium which can be utilized to prepare particular derivatives therefrom.

A preparation for 4-hydroxystyrene utilizing 4-acetoxystyrene is reported in a paper entitled "Preparation of Vinyl-phenols and Isopropylphenols", Corson et al., Volume 23, April 1958 *J. Oro. Chem.* In this preparation, 4-acetoxystyrene is saponified in an aqueous system with a large concentration of a base, KOH, to produce an aqueous solution of the potassium salt of 4-hydroxystyrene which is neutralized with acid to precipitate 4-hydroxystyrene. As indicated above, the procedure is not practical or commercially feasible for production of large quantities of 4-hydroxystyrene because the 4-acetoxystyrene and/or the 4-hydroxystyrene is not very stable and readily polymerizes under the aqueous saponification conditions employed therein, which involve high concentrations of soluble base, resulting in poor yields of 4-hydroxystyrene. A more efficient process for producing 4-hydroxystyrene from 4-acetoxystyrene is desired and needed.

An additional method of preparing 4-hydroxystyrene (also know as paravinylphenol) is described for applications related to perfume compositions, and flavoring for food substances in U.S. Pat. No. 4,316,995 to Pittet et al., issued Feb. 23, 1982.

The instant invention provides a method whereby ready polymerization of the 4-acetoxystyrene and/or the 4-hydroxystyrene in the formation of 4-hydroxystyrene is avoided.

SUMMARY OF THE INVENTION

The present invention is directed to a method of preparing 4-hydroxystyrene and more particularly, for preparing 4-hydroxystyrene by reacting 4-acetoxystyrene with a suitable alcohol in the presence of a catalytic amount of a suitable base.

DETAILED DESCRIPTION

The present invention relates to a method of synthesizing 4-hydroxystyrene of the formula

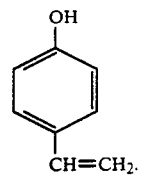

The synthesis of Compound I is made in the following manner. 4-Acetoxystyrene of the formula

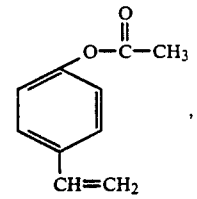

a known compound, which may be synthesized in accordance with the teachings of Corson et al., *J. Org. Chem.* 23 544 (1958), is selected. Compound II is then reacted, via a transesterification, with a suitable alcohol in the presence of a catalytic amount of a suitable base to form Compound I.

A suitable alcohol is an alcohol or a suitable mixture of alcohols having the formula ROH (III), where R is lower alkyl, where the term "lower" means the group it is describing contains from 1 to 6 carbon atoms; the term "alkyl" refers to a straight or branched chain hydrocarbon containing no unsaturation, e.g. methyl, ethyl, propyl, isopropyl, butyl, 2-butyl, n-pentyl, n-hexyl, etc.

The lower the molecular weight and the less branching of the alkyl group, R, the better is the alcohol in terms of the yield of the target Compound I. Preferred alcohols (Compound III) are methanol, ethanol, propanol and isopropanol. A most preferred Compound III or suitable alcohol is methanol and ethanol. It is understood that a suitable mixture of the foregoing alcohols can be employed.

A suitable base includes inorganic bases such as metal hydroxides, preferably an alkali metal hydroxide, e.g. KOH, NaOH, etc., preferably KOH and NaOH; most preferably KOH; an alkali metal alkoxide (an ionic organic base) such as $NaOCH_3$, $KOC(CH_3)_3$, etc., a nitrogen base alkali organic acid salt (an ionic organic base) such as potassium acetate, etc.; and amines (a non-ionic organic base) such as tri-lower-alkylamines, e.g. trimethylamine and triethylamine, etc., which is readily soluble in alcohol III. It is to be understood that a suitable mixture of the foregoing bases can be employed.

By a "catalytic amount" is meant an amount of base which will optimize the yield of Compound I, at the time and temperature selected to run the reaction, with a minimum amount of polymerization of Compound II. This catalytic amount can readily be determined for the suitable alcohol, suitable base, time and temperature selected, by one of ordinary skill in the art without an undue amount of experimentation in the light of the disclosure contained herein. Typically, a catalytic amount of a suitable base, e.g. KOH, ranges from a mole percent of the suitable base to Compound II of from about 0.5 mole percent to about 3 mole percent.

Upon reaction of Compound II with the suitable alcohol, Compound III, e.g. methanol, in the presence of the catalytic amount of the suitable base, e.g. about 0.5 to about 3 mole percent of KOH, Compound I forms in good yields, with a minimum amount of polymerization of Compound II. In addition to Compound I, the acetate ester Compound IV of the formula

forms. The resultant reaction accordingly is a transesterification type reaction. Transesterification reactions typically are catalyzed with acid and usually proceed very well in the presence of acid. It has been found that attempts to react Compound II with a suitable alcohol, Compound III, in the presence of acid leads to polymerization of Compound I and/or Compound II rather than formation of target Compound I. Accordingly, the utilization of the suitable base is critical. It is also critical that only the catalytic amount of suitable base be employed. For example, if large concentrations of the suitable base, e.g. KOH, are employed, such as those concentrations typically employed in aqueous saponification, then again, a great degree of polymerization of Compound II occurs rather than the formation of target Compound I.

The concentration of the suitable alcohol, Compound III, to Compound II, during the reaction therebetween, is in excess of a 1 to 1 molar ratio, typically ranging from about 10 to about 20 times in excess of Compound III to Compound II.

The reaction may be conducted at a temperature typically ranging from about 25° C. to reflux, for a period of time sufficient to complete the reaction. In this regard, the higher the temperature the shorter the reaction time that is necessary. In addition, the greater the catalytic amount employed at a particular temperature the less will be the reaction time. For example with about 0.5 molar percent of the suitable base, e.g. KOH, at reflux temperature, e.g. 65° C. for methanol, the reaction time is typically about 4 hours to get complete reaction of Compound II, whereas at a catalytic amount of about 3 mole percent of the suitable base, e.g. KOH, at the same reflux temperature, the reaction time is typically about 1 to about 2.5 hours to get essentially complete reaction of Compound II.

The acetate ester, Compound IV, e.g. methyl acetate, may be removed during the course of the reaction to drive the reaction and the formation of Compound I to completion. Additionally, resultant salt, e.g. the potassium salt of Compound I, present in the excess suitable alcohol is neutralized, such as for example by the addition of acetic acid, whereafter the excess alcohol (Compound III) is removed from the reaction container, by any conventional manner, as for example by evaporation under reduced pressure; followed by recrystallization of Compound I from a suitable solvent, such as toluene, benzene and mixtures of aromatic hydrocarbons, e.g. benzene, toluene, etc., with a paraffin, such as hexane, petroleum ether, etc., at a temperature ranging from −78° C. to 25° C. In addition, Compound I can be redissolved in a suitable solvent such as an alcohol, e.g. methanol, and reprecipitated from solution by the addition of water to obtain isolated Compound I.

The resultant 4-hydroxystyrene (Compound I) is used in the preparation of coatings, ion exchange resins, for electronic applications, and for food and cosmetic applications, as previously described.

EXAMPLE 1

To a 1000 ml. glass round-bottom flask fitted with a chilled water reflux condenser, thermowell with thermocouple, nitrogen purge, magnetic stirring, and an external heating mantle, a mixture of 200 grams of 4-acetoxystyrene, 500 grams of methanol and 2.5 grams of potassium hydroxide (85% pure by weight with water) was added. The reaction mixture was stirred for 5 minutes while the nitrogen purge removed the oxygen. The reaction mixture was then raised to 65° C., the reflux temperature of methanol. Analysis by capillary gas chromatography showed greater than 99% conversion of the 4-acetoxystyrene to 4-hydroxystyrene after 1 hour and 25 minutes. The reaction mixture was cooled to 30° C. and 2.88 grams of glacial acetic acid dissolved in 10 grams of methanol was added in small portions over 5 minutes to neutralize the KOH. The reaction mixture was stirred for an additional 5 minutes. The methanol and methyl acetate were substantially removed under reduced pressure while maintaining 25°–30° C. The resulting 4-hydroxystyrene was then dissolved in toluene to precipitate any poly(4-hydroxystyrene) which was filtered. The clear solution was then cooled to approximately −70° C. at which time the 4-hydroxystyrene crystallized. The resulting 4-hydroxystyrene was filtered from the toluene and dried on the filter at 25° C. Yield of this single crystallization was 68.2%. Capillary gas chromatographic analysis of the final sample showed greater than 99 wt. % 4-hydroxystyrene.

EXAMPLE 2

To a 1000 ml. glass round-bottom flask fitted with a chilled water reflux condenser, thermowell with thermocouple, nitrogen purge, magnetic stirring, and an external heating mantle, a mixture of 25 grams of 4-acetoxystyrene, 50 grams of methanol and 10 grams of potassium acetate was added. The reaction mixture was stirred for 5 minutes while the nitrogen purge removed the oxygen. The reaction mixture was then raised to 65° C., the reflux temperature of methanol. Analysis by capillary gas chromatography showed greater than 99% conversion of the 4-acetoxystyrene to 4-hydroxystyrene after 4 hours. The 4-hydroxystyrene was not isolated. Contained yield of 4-hydroxystyrene was 96%.

EXAMPLE 3

To a 1000 ml. glass round-bottom flask fitted with a chilled water reflux condenser, thermowell with thermocouple, nitrogen purge, magnetic stirring, and an external heating mantle, a mixture of 25 grams of 4-acetoxystyrene, 50 grams of methanol and 0.85 grams of sodium methoxide was added. The reaction mixture was stirred for 5 minutes while the nitrogen purge removed the oxygen. The reaction mixture was then raised to 65° C., the reflux temperature of methanol. Analysis by capillary gas chromatography showed greater than 99% conversion of the 4-acetoxystyrene to 4-hydroxystyrene after 1 hour. The 4-hydroxystyrene was not isolated. Contained yield of 4-hydroxystyrene was 96%. After 4 hours, the 4-acetoxystyrene conversion was greater than 99% with 86.4% selectivity to 4-hydroxystyrene and 26.6% selectivity to 1-methoxy-1-(4'-hydroxyphenol)ethane.

EXAMPLE 4

To a 500 ml. glass round-bottom flask fitted with a chilled water reflux condenser, thermowell with thermocouple, nitrogen purge, magnetic stirring, and an external heating mantle, a mixture of 100 grams of 4-acetoxystyrene, 200 grams of methanol and 0.35 grams of potassium hydroxide (85% pure, by weight with water) was added. The reaction mixture was stirred for 5 minutes while the nitrogen purge removed the oxygen. The reaction mixture was then raised to 65° C., the reflux temperature of methanol. Analysis by capillary gas chromatography showed greater than 99% conversion of the 4-acetoxystyrene to 4-hydroxystyrene after 3.5 hours. The reaction mixture was cooled to 30° C. and 0.41 g of glacial acetic acid dissolved about 10 g of methanol was added in small portions over 5 minutes to neutralize the KOH. The methanol and methyl acetate was substantially removed under reduced pressure while maintaining 25°-30° C. The resulting 4-hydroxystyrene was then dissolved in toluene to precipitate any poly(4-hydroxystyrene) which was filtered. The clear solution was then cooled to approximately −70° C. at which time the 4-hydroxystyrene crystallized. The resulting 4-hydroxystyrene was filtered from the toluene and dried on the filter at 25° C. Yield of this single crystallization was 71.5%. Capillary gas chromatographic analysis of the final sample showed greater than 99 wt. % 4-hydroxystyrene.

EXAMPLE 5

To a 100 ml. glass round-bottom flask fitted with a chilled water reflux condenser, thermowell with thermocouple, nitrogen purge, magnetic stirring, and an external heating mantle, a mixture of 10 grams of 4-acetoxystyrene, 20 grams of methanol and 5 grams of triethylamine was added. The reaction mixture was stirred for 5 minutes while the nitrogen purge removed the oxygen. The reaction mixture was then raised to 65° C., the reflux temperature of methanol. Analysis by capillary gas chromatography showed 76% conversion of the 4-acetoxystyrene to 4-hydroxystyrene after 3 hours. The 4-hydroxystyrene was not isolated. Contained yield of 4-hydroxystyrene was 76%.

EXAMPLE 6

To a 100 ml glass round-bottom flask fitted with a chilled water reflux condenser, thermowell with thermocouple, nitrogen purge, magnetic stirring, and an external heating mantle, a mixture of 25 grams of 4-acetoxystyrene, 50 grams of methanol and 0.86 grams of sodium methoxide was added. The reaction mixture was stirred for 5 minutes while the nitrogen purge removed the oxygen. The reaction mixture was then raised to 65° C., the reflux temperature of methanol. Analysis by capillary gas chromatography showed greater than 99% conversion of the 4-acetoxystyrene to 4-hydroxystyrene after 1 hour. The 4-hydroxystyrene was not isolated. Contained yield of 4-hydroxystyrene was 96%.

EXAMPLE 7

To a 100 ml. glass round-bottom flask fitted with a chilled water reflux condenser, thermowell with thermocouple, nitrogen purge, magnetic stirring, and an external heating mantle, a mixture of 25 grams of 4-acetoxystyrene, 50 grams of methanol and 0.85 grams of potassium hydroxide (85% pure, by weight with water) was added. The reaction mixture was then raised to 65° C., the reflux temperature of methanol. Analysis by capillary gas chromatography showed greater than 99% conversion of the 4-acetoxystyrene to 4-hydroxystyrene after 1 hour. Selectivity to 4-hydroxystyrene was 94.1%. Selectivity to 1-methoxy-1-(4'-hydroxyphenol)ethane was 5.9%. After 4 hours, selectivity to 4-hydroxystyrene was 73.6% and selectivity to 1-methoxy-1-(4'-hydroxyphenol)ethane was 26.4%. The 4-hydroxystyrene was not isolated.

EXAMPLE 8

To a 100 ml. glass round-bottom flask fitted with a chilled water reflux condenser, thermowell with thermocouple, nitrogen purge, magnetic stirring, and an external heating mantle, a mixture of 25 grams of 4-acetoxystyrene, 50 grams of methanol and 1.0 gram of potassium acetate was added. The reaction mixture was stirred for 5 minutes while the nitrogen purge removed the oxygen. The reaction mixture was then raised to 65° C., the reflux temperature of methanol. Analysis by capillary gas chromatography showed 48.2% conversion of the 4-acetoxystyrene to 4-hydroxystyrene after 4 hours. The 4-hydroxystyrene was not isolated. Contained yield of 4-hydroxystyrene was 48.2%

EXAMPLE 9

To a 100 ml. glass round-bottom flask fitted with a chilled water reflux condenser, thermowell with thermocouple, nitrogen purge, magnetic stirring, and an external heating mantle, a mixture of 10 grams of 4-acetoxystyrene, 20 grams of methanol and 5 grams of pyridine was added. The reaction mixture was stirred for 5 minutes while the nitrogen purge removed the oxygen. The reaction mixture was then raised to 65° C., the reflux temperature of methanol. Analysis by capillary gas chromatography showed 5.4% conversion of the 4-acetoxystyrene to 4-hydroxystyrene after 3 hours. The 4-hydroxystyrene was not isolated. Contained yield of 4-hydroxystyrene was 5.4%.

While specific reactants and reaction conditions are described in the Examples of preferred embodiments above, one skilled in the art will be able to make modifications and adjustments which are obvious extensions of the present invention. Such obvious extensions and equivalents are intended to be within the scope of the present invention, as demonstrated by the claims which follow.

We claim:

1. A method for preparing 4-hydroxystyrene, which comprises:
    reacting 4-acetoxystyrene with an alcohol having the formula ROH, wherein R is an alkyl having from 1 to 6 carbon atoms; in the presence of a catalytic amount of a base selected from the group consisting of metal hydroxides, alkali metal alkoxides, nitrogen base alkali organic acid salts, alkyl and aromatic amines, and combinations thereof; to form the 4-hydroxystyrene.

2. The method as defined in claim 1 wherein said alcohol is one selected from the group consisting of methanol, ethanol, propanol, isopropanol and any suitable mixture of the foregoing.

3. The method as defined in claim 2 wherein said alcohol is selected from the group consisting of methanol, ethanol and a mixture of the foregoing.

4. The method as defined in claim 1 wherein said base is selected from the group consisting of potassium hydroxide, sodium hydroxide, K₂CO₃, triethylamine, trimethylamine,

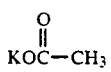

NaOCH₃, KOCH₃, tripropylamine, pyridine, potassium-tertiary-butoxide, and any suitable mixture of the foregoing.

5. The method as defined in claim 4 wherein said base is potassium hydroxide.

6. The method as defined in claim 1 wherein said catalytic amount is from about 1.5 molar percent to about 3.6 molar percent based upon the concentration of said base to said 4-acetoxystyrene.

7. The method as defined in claim 6 wherein said alcohol is methanol, said base is KOH and said reaction is carried out at a temperature of about 25° C. to about 65° C. for about 1 to about 6 hours.

* * * * *